US012605042B2

(12) United States Patent
Quensel et al.

(10) Patent No.: US 12,605,042 B2
(45) Date of Patent: Apr. 21, 2026

(54) ENDOSCOPE

(71) Applicant: AMBU A/S, Ballerup (DK)

(72) Inventors: Ulf Quensel, Ystad (SE); Barbara Tornaghi, Monza (IT); Andrea Besana, Seveso (IT); Felix Andreas Graw, Augsburg (DE)

(73) Assignee: AMBU A/S, Ballerup (DK)

( * ) Notice: Subject to any disclaimer, the term of this patent is extended or adjusted under 35 U.S.C. 154(b) by 580 days.

(21) Appl. No.: 18/097,914

(22) Filed: Jan. 17, 2023

(65) Prior Publication Data

US 2023/0248212 A1 Aug. 10, 2023

(30) Foreign Application Priority Data

Feb. 7, 2022 (EP) .................................... 22155415

(51) Int. Cl.
*A61B 1/005* (2006.01)
*A61B 1/00* (2006.01)

(52) U.S. Cl.
CPC ...... *A61B 1/00066* (2013.01); *A61B 1/00045* (2013.01); *A61B 1/0052* (2013.01)

(58) Field of Classification Search
CPC .............. A61B 1/00066; A61B 1/0052; A61B 1/00121; A61B 1/00045; A61B 1/00147; A61B 2017/00442; A61B 2017/00438
See application file for complete search history.

(56) References Cited

U.S. PATENT DOCUMENTS

| | | | |
|---|---|---|---|
| 5,152,278 A | 10/1992 | Clayman | |
| 2002/0026096 A1* | 2/2002 | Motoki | .............. A61B 1/00042 |
| | | | 600/117 |
| 2005/0070885 A1 | 3/2005 | Nobis et al. | |
| 2006/0287575 A1 | 12/2006 | Onoda et al. | |
| 2006/0293565 A1 | 12/2006 | Uchimura et al. | |
| 2007/0027361 A1* | 2/2007 | Uchimura | ............ A61B 1/0052 |
| | | | 600/152 |
| 2007/0038023 A1 | 2/2007 | Uchimura et al. | |
| 2008/0015631 A1* | 1/2008 | Lee | ..................... A61B 1/0052 |
| | | | 606/205 |

(Continued)

FOREIGN PATENT DOCUMENTS

| | | |
|---|---|---|
| JP | 57-039826 A | 3/1982 |
| JP | 57-139301 U | 8/1982 |

(Continued)

OTHER PUBLICATIONS

European Search Report for EP Patent Application No. 22155415.7, Issued on Jul. 1, 2022, 7 pages.

*Primary Examiner* — Michael J Carey
*Assistant Examiner* — Olivia Grace Starkey
(74) *Attorney, Agent, or Firm* — Faegre Drinker Biddle & Reath LLP

(57) ABSTRACT

An endoscope including a handle, a wing, and an insertion cord. The handle includes a proximal operating section, a distal transition section, and an intermediate gripping section. The wing extends from the operation section and is selectively rotatable between an active position in which the wing extends along the handle to provide a hand space between the handle and the wing and a passive position in which the wing is moved away with respect to the handle positioning a free end of the wing at a second, larger, distance to the handle.

20 Claims, 5 Drawing Sheets

(56)          References Cited

U.S. PATENT DOCUMENTS

| | | | |
|---|---|---|---|
| 2009/0287047 A1 | 11/2009 | Onoda et al. | |
| 2010/0312055 A1* | 12/2010 | Konstorum | A61B 1/00066 |
| | | | 600/131 |
| 2013/0012781 A1 | 1/2013 | Kaneko | |
| 2016/0089003 A1* | 3/2016 | Morimoto | A61B 1/00177 |
| | | | 600/107 |
| 2017/0086651 A1 | 3/2017 | Sato et al. | |
| 2017/0172386 A1 | 6/2017 | Okamoto | |
| 2017/0209025 A1 | 7/2017 | Imai | |
| 2017/0215696 A1 | 8/2017 | Harrah et al. | |
| 2018/0160883 A1* | 6/2018 | Viebach | A61B 1/00042 |

FOREIGN PATENT DOCUMENTS

| | | | |
|---|---|---|---|
| JP | 06-304122 A | 11/1994 | |
| JP | 2002-112945 A | 4/2002 | |
| JP | 2002-186576 A | 7/2002 | |
| JP | 2002-282199 A | 10/2002 | |
| JP | 2005-312687 A | 11/2005 | |
| JP | 2006-149880 A | 6/2006 | |
| WO | 2021/219832 A1 | 11/2021 | |

* cited by examiner

ENDOSCOPE

CROSS-REFERENCE TO RELATED APPLICATIONS

This application claims priority from and the benefit of European Patent Application No. EP 2215 5415, filed Feb. 7, 2022; said application is incorporated by reference herein in its entirety.

TECHNICAL FIELD

The present disclosure relates to endoscopes, and in particular flexible endoscopes.

BACKGROUND

Endoscopes are known and used for visual navigation into, and examination and diagnosis of, hollow organs and body cavities, as well as, optionally, to assist in surgery, e.g. for a targeted tissue sampling. Endoscopes include procedure-specialized endoscopes, such as bronchoscopes, gastroscopes and duodenoscopes. An endoscope typically comprises a handle at the proximal end to be gripped by an operator and a flexible elongated insertion cord terminated at the distal end in a tip part at the end of a highly bendable, e.g. articulated, bending section, controllable by the operator. The tip part normally comprises a visual inspection means such as a camera, and illumination means such as LED's or exit apertures of light fibres and whatever optics are needed in that connection. An example of such endoscopes is described in commonly-owned International Patent Publication No. WO2021219832, which relates to a duodenoscope and is incorporated by reference herein.

The controllable bending section is normally an articulated section at the distal tip of the elongated insertion cord that can be controlled by the operator via control knobs arranged on the handle.

Thus, using the controls allows the operator to advance the distal tip of the endoscope to a desired location by means of a series of actions involving, inter alia, bending the bending section in a desired direction, advancing the elongated insertion cord and turning the elongated insertion cord by turning the handle which is rigidly connected thereto. Navigating a tortuous path of bends and turns to a location of interest may subject the elongated insertion cord including the distal controllable bending section to substantial forces including compression, torsion, and bending. The main body of the elongated insertion cord is generally only bendable enough to follow the direction taken by the bending section and configured to transmit the longitudinal pushing forces and rotary torsional forces from the handle to the distal end of the elongated insertion cord in order to allow these maneuvers.

The endoscope may be connected to a display device to display images from the tip to allow the operator to find the way through the insertion maneuvers as well as during any procedure at a target location. The display device may also include other functionalities, such as power supply for the endoscope or supply of light through the light guides, all depending on the actual type and construction of the endoscope. This connection is normally referred to as an umbilical.

The umbilical typically extends from the proximal end of the handle in a cross-wise direction as compared to the overall length of the endoscope, i.e. perpendicular to the longitudinal axis of the insertion cord when the insertion cord is in an unbent state extending straight as a natural extension of the handle towards the distal end of the endoscope.

Procedures using endoscopes can be relatively time consuming, such as one hour or even more, and the position of the handle may be awkward after insertion of the insertion cord into the patient. It may stressful or even impossible for the operator to maintain a firm grip throughout the procedure. For example, in case of a colonoscopy, the operator inserts the insertion cord of a colonoscope through the rectum and colon of a patient. Peristaltic movements of the colon may, however, work against forwarding the colonoscope, so the operator must hold and push the insertion cord forward with one hand (typically the right hand) while holding the handle with the another hand (typically the left hand). Further, the operator must at the same time operate the control wheel to direct the distal end of the insertion cord in a desired direction, which is typically done using fingers of the hand holding the handle (typically the left hand). Another example is insertion of a duodenoscope, e.g. for performing an Endoscopic Retrograde Cholangiopancreatography (ERCP), which is a very specialized and sensitive endoscopic procedure to diagnose and treat issues with the pancreatic duct, bile duct, and pancreas, where it is necessary to hold the duodenoscope in a specific position for an extended period at a treatment site, while potentially adjusting position of the distal end portion of the insertion cord by operating the control wheel, which again typically is done with fingers of the hand holding the handle (typically the left hand).

The operator must be highly skilled and experienced, and as such is in high demand. The type of work is straining, intensive and repeated, which may give rise to repetitive strain injury. Further, the ergonomics of known endoscopes are not ideal for all operators. This means that some operators may have difficulties in performing their job or may face attrition over time JP-2006-149880 suggests to provide a handle with a detachable strap. This detachable strap would seem to engage the back of the hand, possibly allowing the operator to loosen the grip. The addition of a strap and strap connections at the handle increases complexity and cost, which is undesirable, particularly in single-use endoscopes, and further the strap may be too constraining for some operators, e.g. having large hands.

U.S. Patent Publication No. 2006/0287575 discloses an endoscope where the umbilical is connected to the endoscope at a location in the proximity of the tool entry port on the transition section of the handle between the gripping section and the insertion cord. A fixed hook is arranged in front of the part of the gripping section where the operator's fingers (apart from the thumb) engage the handle and buttons and prevents the operator from dropping the handle if the grip is loose. The hook may however be in the way when operating the endoscope, and may be too constraining for some operators, e.g. having large hands.

BRIEF DESCRIPTION OF THE DISCLOSURE

The objective of the present disclosure is to provide an endoscope with features that eliminate or at least reduce the disadvantages of known endoscopes and suitably deal with the problems described above. In particular, it is an object of the present disclosure to present an endoscope with good ergonomics allowing the operator to loosen the grip around the handle during a procedure. According to the first aspect of the disclosure, this object is achieved by an embodiment of an endoscope comprising, at the proximal end, a handle adapted to be gripped by a hand of an operator, the handle comprising a proximal operating section, a distal transition section from which an insertion cord extends towards the distal end of the endoscope, an intermediate gripping section adapted to be gripped by palm and fingers of said hand of the operator, and a wing connected to and extending from the operating section and having a free end, wherein the wing is selectively movable between an active position in which the wing extends along the handle with the free end at a first distance to the handle to provide a hand space between the handle and the wing, and a passive position in which the wing is moved away with respect to the handle positioning the free end at a second, larger distance to the handle.

Hereby a versatile solution is achieved in that the position of the wing can be moved to meet operator needs or preferences. Some operators may prefer to have the wing in one position during a certain part of the procedure, and then move the wing to another position during another part of the procedure.

According to a variation of the present embodiment, in the active position, a minimum gap between the wing and the handle is in the range of 25 to 35 mm. This range is considered feasible for a wide range of operators with different hand size. This range is considered to fulfil the preferences for 5 percentile female operators to 95 percentile male operators with regard to thickness of their hands.

According to another variation of the present embodiment, the wing is rotatably connected to the handle to be movable through a rotary motion path about a wing rotation axis.

According a further variation of the present embodiment, the length of the wing is in the range between 40 mm and 100 mm preferably between 50 mm and 85 mm. Lengths in this interval have been found to cover most hand sizes of operators, while still being comfortable for all.

According to another variation of the present embodiment, the insertion cord defines a longitudinal axis and said rotation axis is perpendicular to said longitudinal axis of the insertion cord.

According to yet another variation of the present embodiment, the operating section comprises at least one rotary operating member rotatable about an operating member axis.

According to another variation of the present embodiment, the rotary operating member is located on an opposite side of the handle as seen from the wing.

According to another variation of the present embodiment, the wing rotation axis coincides with the operating member axis.

According to another variation of the present embodiment, at least one predetermined arresting position is provided along the rotary motion path.

According to another variation of the present embodiment, the tip of the wing is resiliently deflectable away from the handle. It has been found that the resiliently deflectable wing increases comfort because it allows the back of the hand to be supported while at the same time the resilient deflection keeps the localized pressure on the back of the hand down.

According to another variation of the present embodiment, the wing comprises a core member with a Shore A hardness in the range of 75 to 120. This has been found to achieve a comfortable pressure on the back of the hand. This is in particular the case if, according to a further embodiment of the first aspect of the disclosure, the core member is covered by a softer coating. Accordingly, in a variation of the present embodiment, this softer coating has a Shore A hardness in the range from 40 to 60, preferably approximately 50.

The variations of the present embodiment described above may be combined to achieve additional variations thereof.

In one further variation the wing is rotatably connected to the handle, a minimum gap between the wing and the handle is in the range of 25 to 35 mm, and a rotary operating member is located on an opposite side of the handle as seen from the wing. In one example of the present variation, the tip of the wing is resiliently deflectable away from the handle. In another example of the present variation, the tip of the wing is not resiliently deflectable away from the handle.

In another further variation the wing is rotatably connected to the handle, the wing comprises a core member with a Shore A hardness in the range of 75 to 120 and the core member is covered by a softer coating having a Shore A hardness in the range from 40 to 60. In one example of the present variation, a minimum gap between the wing and the handle is in the range of 25 to 35 mm, and a rotary operating member is located on an opposite side of the handle as seen from the wing. In another example of the present variation, the minimum gap is greater than 35 mm.

According to a second aspect of the disclosure, the object is achieved by a visualization system comprising a display device and an endoscope according to the first aspect connectable to said display device.

BRIEF DESCRIPTION OF THE DRAWINGS

The disclosure will now be made in greater detail based on non-limiting exemplary embodiments and with reference to the schematic drawings on which.

DETAILED DESCRIPTION

In the following the term "distal" refers to a position farthest away from the operator, whereas the term "proximal" refers to the end closest to the operator when using the endoscope in a patient.

Unless otherwise noted, components having the same structure and/or function are denoted with the same numerals throughout the several figures, embodiments, variations, and examples thereof.

Figure 1A:
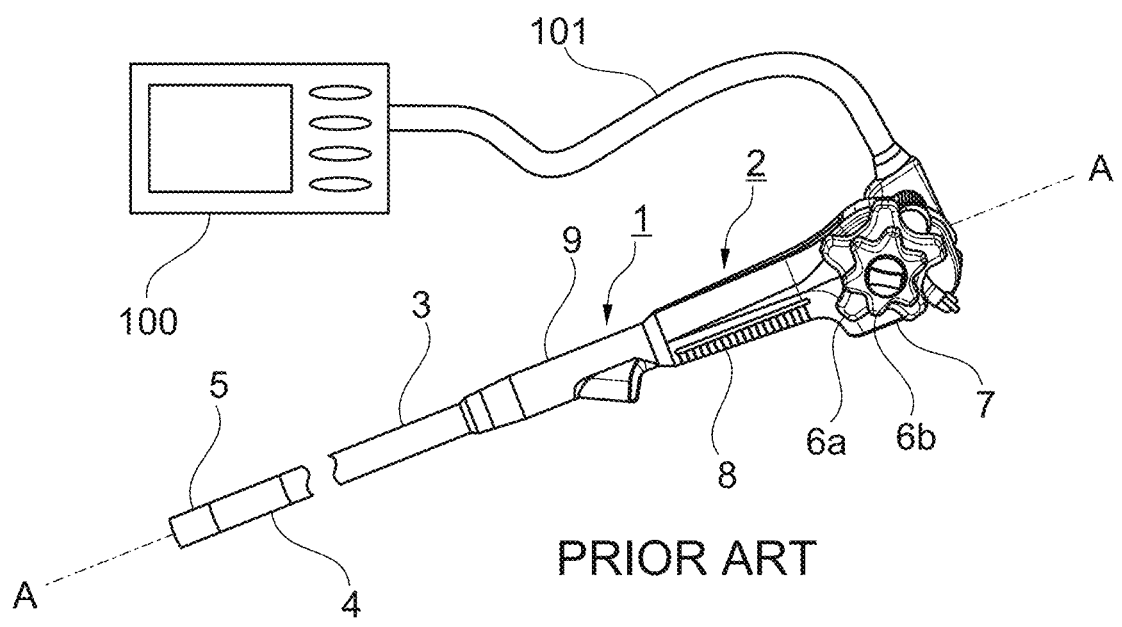
FIG. 1A shows a system of a display device and a prior art endoscope connected to the display device via an umbilical.
Figure 1B:
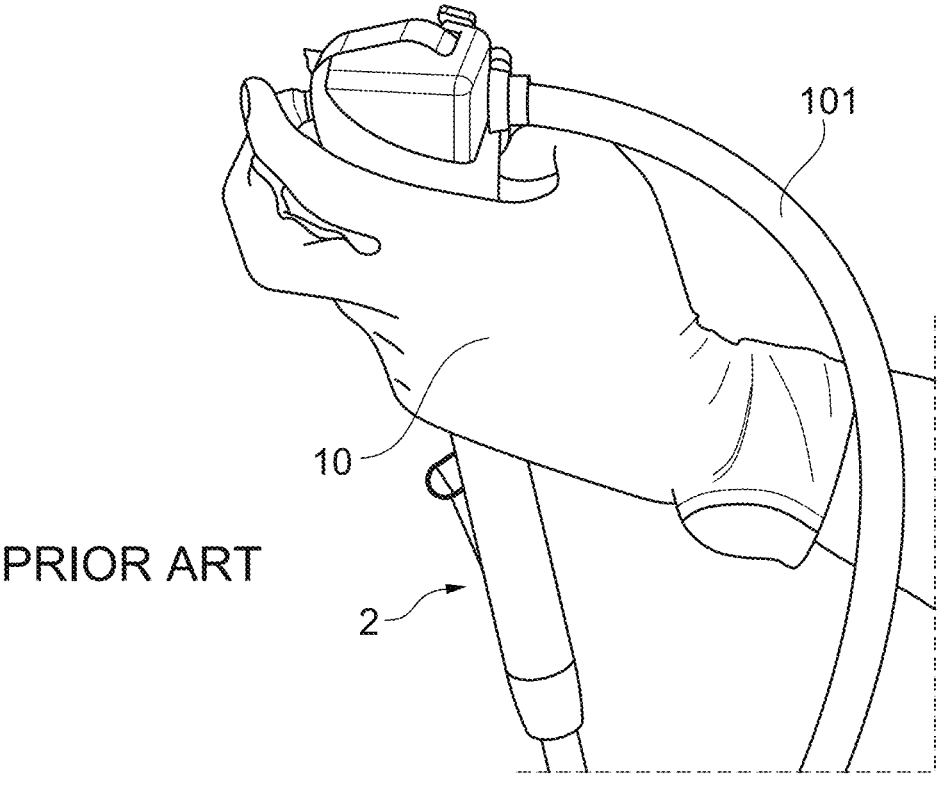
FIG. 1B illustrates the endoscope of FIG. 1A held by an operator.

Turning first to FIGS. 1A and 1B, a prior art endoscope 1 is shown. The endoscope 1 is part of a system also comprising a display device 100 to which the endoscope 1 may be connected using an umbilical 101 as shown. The endoscope comprises a handle 2 forming the proximal end of the endoscope and an insertion cord 3 extending from the handle towards the distal end of the endoscope 1. The insertion cord 3 comprises a highly flexible bending section 4 terminating in a tip housing 5 at the distal end of the endoscope 1. The bending section 4 may be controlled by an operator using one or more rotary operating members 6a, 6b such as wheels or turn knobs arranged at an operating section 7 forming the most proximal part of the handle 2. The handle furthermore comprises a gripping section 8 adapted to be gripped by a hand 10 of an operator. The handle 2 furthermore comprises a transition section 9 from which the insertion cord 3 extends. The gripping section is thus located between the operating section and the transition section as seen in the direction along the longitudinal axis A-A of the endoscope 1. The longitudinal axis is defined by the centre axis of the insertion cord 3 in a straight, unbent, state. This definition applies to the remainder of the present disclosure too. The handle 2 also has an elongate shape generally aligned with the centre axis of the insertion cord 3 so that at least some parts of the handle 2, e.g. of the transition section 9, exhibit rotational symmetry about the longitudinal axis A-A. As will be noted the umbilical 101 extends in a crosswise direction to the longitudinal axis A-A, but with an off-set, i.e. not intersecting the longitudinal axis A-A. In the illustrated example of FIGS. 1A and 1B the umbilical 101 extends backward from the handle 2 at the left-hand side thereof. As to the references up, down, left, right, front, and back the presumption is that the endoscope 1 is held in front of the operator standing with the lower left arm straight and gripping the gripping section 8 of the endoscope, and the insertion cord 3 pointing vertically down, i.e. that the axis A-A is vertical. The references up, down, left, right, front, and back, as applied to the endoscope 1, are then used in the same manner as they would normally apply to the standing operator as illustrated in FIG. 1B. This convention applies throughout the disclosure.

Figure 2:
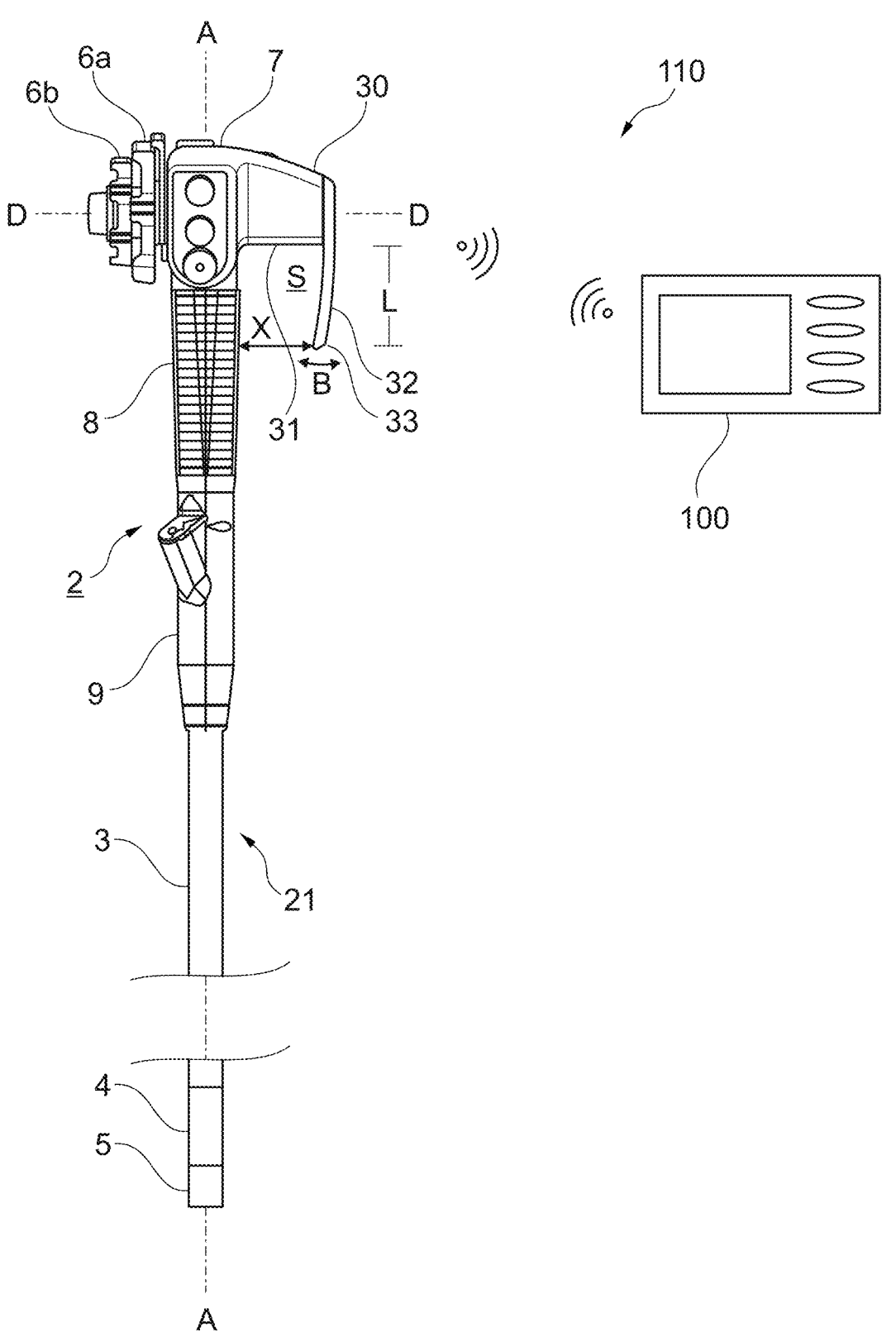
FIG. 2 shows a visualization system including an embodiment of an endoscope according to the disclosure and a display device, the endoscope including a handle and a wing.

Turning now to FIG. 2, an embodiment of a visualization system 110 including an endoscope according to the present disclosure, denoted by numeral 21, is presented along with a display device 100. Accordingly, the endoscope 21 comprises a handle 2 forming the proximal end of the endoscope 21 and an insertion cord 3 extending from the handle 2 towards the distal end of the endoscope 21. The insertion cord 3 comprises a highly flexible bending section 4 and a tip housing 5 at the distal end of the endoscope 21. The bending section 4 may be controlled by an operator using one or more rotary operating members 6a, 6b such as wheels or turn knobs arranged at an operating section 7 forming the most proximal part of the handle 2. The bending section 4 may be controlled via pull wires (not shown) running through the insertion cord from the operating members to the bending section 4. The handle furthermore comprises a gripping section 8 adapted to be gripped by a hand of an operator. The handle 2 additionally comprises a transition section 9 from which the insertion cord 3 extends. The gripping section 8 is thus located between the operating section 7 and the transition section 9 as seen in the direction along the longitudinal axis A-A of the endoscope 21. The longitudinal axis is defined by the centre axis of the insertion cord 3 in a straight, unbent, state. The handle 2 also has an elongate shape generally aligned with the centre axis of the insertion cord 3 so that at least some parts of the handle 2, e.g. of the transition section 9, exhibit rotational symmetry about the longitudinal axis A-A.

The display device 100 is schematically illustrated. An umbilical 101 is not shown, as it may extend from many various places on the endoscope 21 or may even be entirely omitted if the endoscope 21 is self-contained in terms of power supply etc. and communication to the display device 100 is wireless, as schematically indicated.

The operating section 7 comprises a crosswise protrusion 30 on the side opposite the operating members 6a, 6b. The protrusion 30 has a rounded lower surface 31 adapted to rest on the web between the operator's thumb and index finger of the left hand. The remaining fingers and possibly the index finger will curve around the gripping section 8 to the front in order to grip the handle 2. Connected to the protrusion is a wing 32. In the illustrated, active, position, the wing 32 and the gripping section 8 form a space S to accommodate part of the hand gripping the gripping section 8, and the wing 32 is adapted to engage the back of the hand gripping the gripping section 8. The space defines a gap provided between the wing 32 and the gripping section 8. The wing can be parallel to the gripping section or may have a minimum distance X at a position anywhere along the length of the wing 32, such as at the free end 33 as illustrated. In the illustrated example the wing 32 is curved or bent slightly towards the handle. Suitable values for this bend are considered to be in the range of 5-15 degrees. As shown, a portion of the wing 32 proximal to the protrusion 30 is substantially straight and the bend begins intermediate the length L of the wing 32, for example between 40-60% of the length L. Alternatively, the bend may begin closer to the protrusion 30 than 40% of the length L. It may, however, be preferred that the minimum distance is not at the free end 33 to facilitate insertion of the hand in the gap from below. Instead, the minimum distance may be intermediate the length L of the wing 32, with the free end 33 disposed further away from the handle than the location of the minimum distance. The wing 32 forms a hook preventing the palm of the hand from moving too far away from the gripping section 8 if the operator loosens the grip e.g. by straightening the curved gripping fingers. This is in particular relevant if the handle 2 is not in the shown vertical position but has to be held in e.g. a horizontal position with the right-hand side down over a longer period during a procedure, where the operator might need to relax the gripping fingers.

The wing 32, preferably, has some lateral resilient flexibility as indicated with the double arrow B in order not to press too hard on the back of the operator's hand, and may furthermore have a soft comfortable surface, i.e. softer than the material from which the handle 2 or at least the gripping section 8 thereof is made. Resilient flexibility is a property, which is achieved by combination of material, construction and geometry (e.g. thickness) of the wing. If the wing 32 or at least a core member thereof is made from a material with a Shore A hardness of 75-120, e.g. a hard material, preferably silicone, the desired resiliency may be provided for a wing shaped as illustrated. If the wing 32 is thick, a relatively softer material should be used, and if the wing 32 is thin, a relatively harder material should be used. The core could also comprise the same material as the handle 2, e.g. PP and/or ABS. On the more hard and rigid core, providing the resilient flexibility of the wing 32, a softer, more comfortable, outer layer may be provided. This outer layer could also comprise silicone, albeit with a lower Shore A hardness in the range from 40 to 60, preferably approximately 50. Thus, in one example, the wing comprises a core and an outer layer, the core having a shore-A hardness in the range from 40 to 60, preferably approximately 50, and the core having a Shore-A hardness of 75-120.

The length L of the wing 32, i.e. the part extending from the protrusion 30, is in the range between 40 mm and 100 mm, preferably between 40 mm and 85 mm, preferably between 50 mm and 85 mm, and even more preferrably between 40 and 70 mm. This has been found to cover and be comfortable and yield effective support for most operators' hands, be it of a bigger man with a hand width of e.g. 105 mm or a smaller woman with a hand width of e.g. 65 mm.

The horizontal position described above is, however, not the only awkward position in which the handle 2 may need to be held during a procedure.

Figure 3:
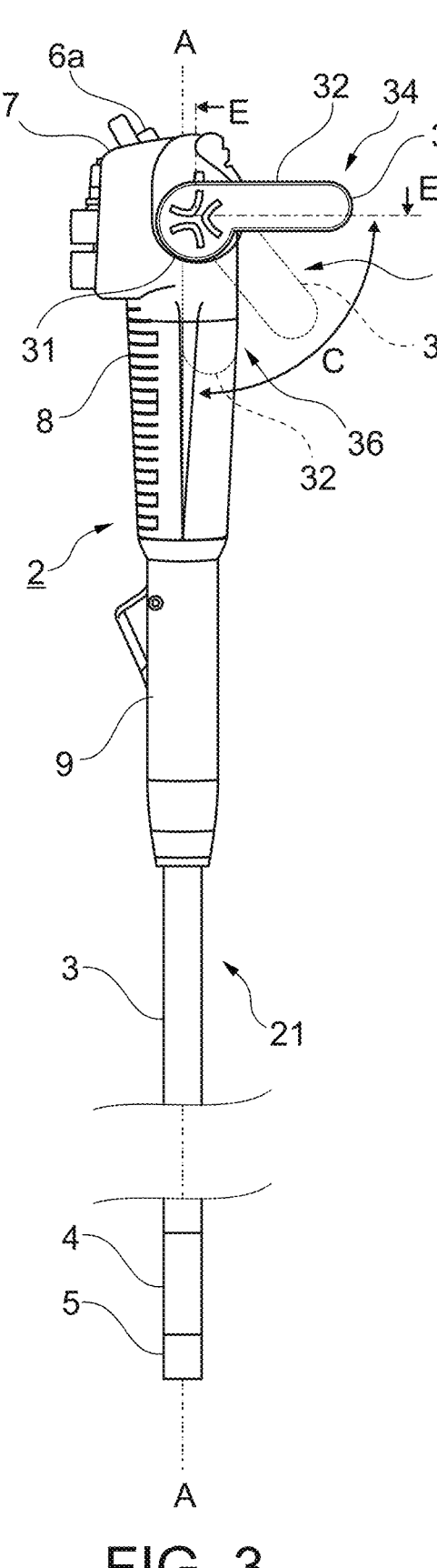
FIG. 3 shows a side view of the endoscope of FIG. 2.

This is solved by the fact that the wing 32 is not fixed as a clip on the handle 2, but instead is movable through a rotary motion path as indicated by the double arrow C in FIG. 3 about a wing rotation axis D-D as seen in FIG. 2. FIG. 3 illustrates various positions of the wing 32, namely an inactive (or second) position 34, in which the wing 32 is rotated away from gripping section 8 (i.e. a horizontal position in the illustration), an intermediate position 35 (with dashed contour), in which the wing is rotated partially away from the gripping section 8, and an active (or first) position 36 (with dashed contour), in which the wing 32 is more or less parallel with the gripping section 8, corresponding to the position of the wing 32 in FIG. 2. It should be noted that although the angle of the rotary path C is shown as 90° between vertical and horizontal other angles could be envisaged. The first arresting position may be at most 90 degrees from the second arresting position along a rotary motion path. This is just one variant among the numerous modifications the skilled person will identify to the exemplary embodiment described without departing from the scope of the claims. The first arresting position may be at greater than 90 degrees from the second arresting position along a rotary motion path, for example, however 90 degrees allows the operator to remove their hand outwardly from the handle.

The wing rotation axis D-D is preferably perpendicular to the longitudinal axis A-A of the endoscope. The wing rotation axis D-D may intersect the longitudinal axis A-A or it may have a slight off-set. The wing rotation D-D axis is preferably parallel to an operating member axis, i.e. the rotary axis of the rotary operating member 6a and/or rotary operating member 6b. They may even coincide as in the embodiment illustrated. Irrespective of whether the axes are parallel or even coincide, it is preferred that the rotary operating member 6a, 6b is located on an opposite side of the handle 2 as seen from the wing 32 to provide good access to the rotary members 6a, 6b for the operator's right hand without being hindered by the wing 32.

As mentioned, the wing 32 is movable through a number of positions, this may be an infinite number, where the wing 32 held in a position chosen at will by the operator and held there, e.g. by friction between the wing 32 and suitable parts of the handle. The force to be applied to the tip of the wing 32 in order to overcome friction and turn the wing 32 should preferably be in the range of 10-15 N in order to prevent the operator form inadvertently rotating the wing 32 during procedure.

The first position may be an arresting position, in which the wing extends along the handle with the free end at a first distance to the handle to provide a hand space between the handle and the wing. The wing may be parallel to the handle in the first arresting position. A force greater than necessary to overcome friction may be required to move the wing from the first arresting position. A biasing mechanism, such as a combination of a recess and mating protrusion, may be used to create the greater force requirement. A resilient tab may also be used without a mating recess. The resilient tab may be located on the wing or the handle and protrudes from a surface of the protrusion 30 (e.g. end-face 40) or a surface of the wing 32 (e.g. inner surface 52). The resilient tab may, optionally, by the use of force, recede into a recess, in which case the recess and the resilient tab are positioned in one or the other of the wing and the handle.

The second position may, but does not need to, be an active or arresting positon. In the second position the wing is moved away with respect to the handle positioning the free end at a second distance to the handle, the second distance being larger than the first distance. The wing is selectively movable between the first arresting position and the second position.

The first arresting position may be defined by a protrusion and a recess, one of the protrusion or the recess located on the handle and the other of the protrusion or the recess located on the wing. Thereby, as used herein, mating is intended to mean that the protrusion and recess are on two components, the handle and the wing.

The first arresting position may be at most 120 degrees from the second position along a rotary motion path, preferrably at most 100 degrees, and most preferrably at most 90 degrees. The second position may comprise a second arresting position. The second arresting position may be defined by a protrusion and a recess, one of the protrusion or the recess located on the handle and the other of the protrusion or the recess located on the wing. The first arresting position may be at most 120 degrees from the second position along a rotary motion path, preferrably at most 100 degrees, and most preferrably at most 90 degrees from the second arresting position along a rotary motion path.

There may also or instead be a finite number of predetermined arresting positions provided by mating protrusions and recesses on opposing surfaces of the protrusion 30 and the wing 32, the mating protrusions mating as the wing 32 is rotated along the rotary motion path C. In one example, protrusions on the wing 32 elastically click into matching recesses provided in the handle 2, or vice versa. The force, referred to as retention force, to be applied to the tip of the wing 32 for the wing 32 to leave these arresting positions should preferably exceed the 10-15 N mentioned above. In all cases the movable wing 32 allows the operator to adapt the position of the wing 32 with respect to the handle 2, so that the mating protrusions and recesses allow for support of the handle in many different orientations, in turn allowing the operator to relax the grip during extended procedures.

Figure 4:
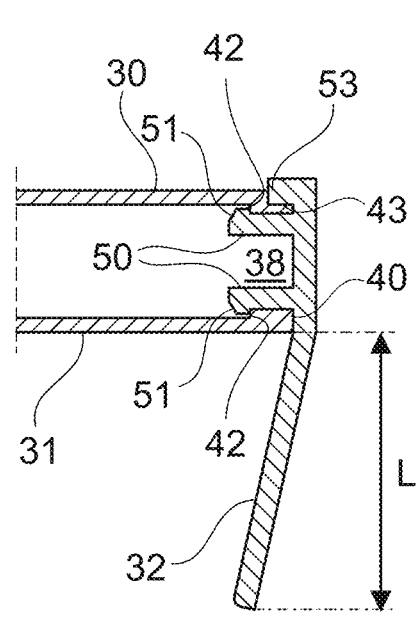
FIG. 4 is a schematic section E-E of FIG. 3.

FIG. 4 is section E-E of FIG. 3 schematically illustrating an example of mounting of the wing 32 to the protrusion 30. The wing 32 comprises resilient legs 50 with hooks 51. The legs 50 enter an opening 38 at the end of the protrusion 30 defined by a wall 31 of the protrusion 30, the wall having an end-face 40, and the hooks 51 engage shoulders 42 at the end of the protrusion 30, thereby restricting disengagement of the wing 32 from the protrusion 30. The wing has an inner surface abutting the end-face 40. The end-face 40 and the inner surface may be provided with rough surfaces to increase friction. The combination of the friction and the dimensions of the protrusions and hooks can provide some of the retention force. The rough surfaces can comprise texture in the form of micro or macro apertures and protrusions. The apertures and protrusions can comprise spheres, lines, geometrical shapes such as hexagons and rectangles, and other known micro and macro apertures and protrusions. The retention force provided by the textures should, in combination with the mating protrusions and recesses that define the arresting positions, not exceed 10-15 N. In an example of a mating protrusion and recess, the wing 32 has a tab 53 engaging a recess, or notch, 43 at a shoulder 42, thereby providing the arresting position 36.

Figure 5:
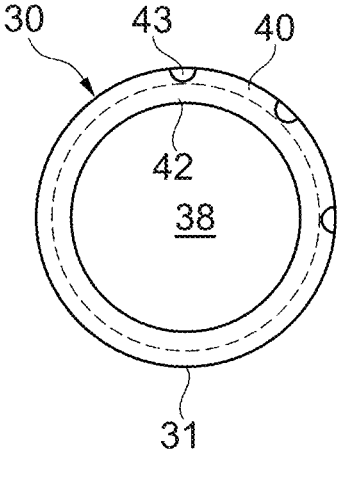
FIGS. 5 and 6 show the handle and the wing according to a variation of the endoscope of FIG. 2.
Figure 6:
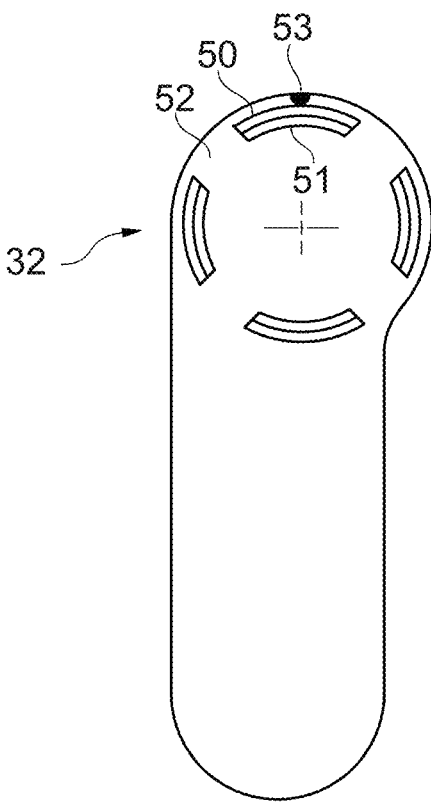

FIGS. 5 and 6 show a mating protrusion 53 and recesses 43. As shown, the recesses 43 extend inwardly from the surface 31 and the protrusion 53 extends toward the handle from the wing's inner surface 52 past the end-face 40. Thusly, the mating is in the radial direction. As indicated before, the locations of the recesses and protrusions that form the arresting positions can be switched and even mixed between the end-face and the inner surface. Additional protrusions 53 and recesses 43 can be provided to increase the retention force. In a variation of the present embodiment, protrusions can extend radially inwardly from a wall surrounding the resilient legs 50, and the recesses 43 extend inwardly from the surface 31 without extending to the end-face 40.

Figure 7:
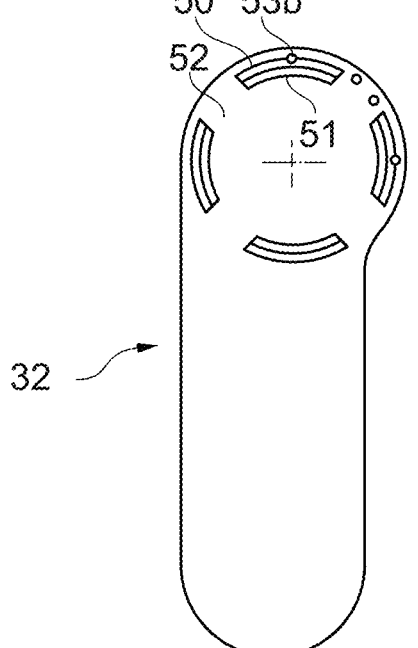
FIGS. 7 and 8 show the handle and the wing according to another variation of the endoscope of FIG. 2.
Figure 8:
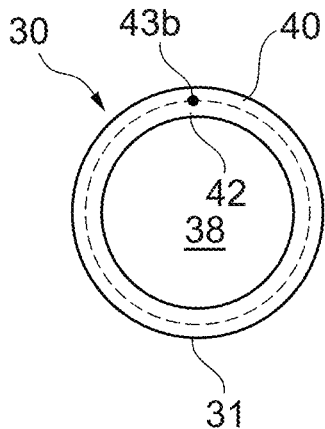

FIGS. 7 and 8 show mating recesses 53*b* and a protrusion 43*b* illustrating another variation of the present embodiment. As shown, the protrusion 43*b* extends longitudinally (along the length of the protrusion 30) away from the handle from the end-face 40 and the recesses 53*b* extend longitudinally from the inner surface 52 away from the handle. Thusly, the mating is in the longitudinal direction. As indicated before, the locations of the recesses and protrusions that form the arresting positions can be switched and even mixed between the end-face and the inner surface. Additional recesses 53*b* and protrusions 43*b* can be provided to increase the retention force.

Figures 9A, 9B, 9C:
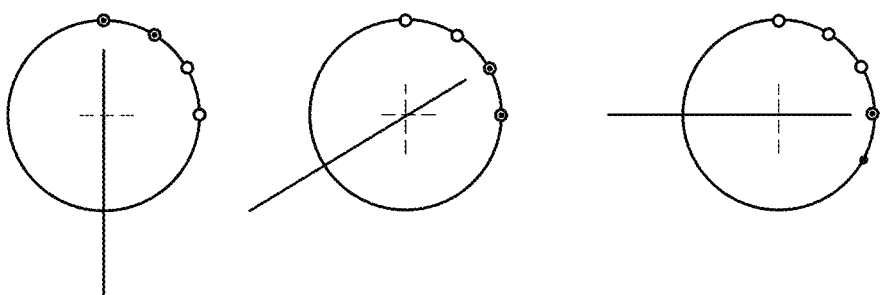
FIGS. 9A, 9B, and 9C are schematic diagrams illustrating three positions of the wing relative to the handle.

FIGS. 9A, 9B, and 9C illustrate a variation of the present embodiment showing four recesses and two protrusions. In the first position of the wing 32, shown in FIG. 9*a*, the two protrusions engage or mate with two recesses. In an intermediate position of the wing 32, shown in FIG. 9*b*, the two protrusions engage two different recesses. In the second position of the wing 32, shown in FIG. 9*c*, one of the two protrusions engages a recess and the other does not. The recesses are shown equally spaced at 22.5 degrees from each other but this is not a necessity, other spacing is also possible.

The following items are further variations and examples of the embodiments described with reference to FIGS. 1A to 9C.

1. An endoscope comprising at the proximal end a handle adapted to be gripped by a hand of an operator, the handle comprising a proximal operating section, a distal transition section from which an insertion cord extends towards the distal end of the endoscope, an intermediate gripping section adapted to be gripped by palm and fingers of said hand of the operator, and a wing connected to and extending from the operation section and having a free end, wherein the wing is selectively movable between an active position in which the wing extends along the handle with the free end at a first distance to the handle to provide a hand space between the handle and the wing, and a passive position in which the wing is moved away with respect to the handle positioning the free end at a second, larger distance to the handle.

2. An endoscope according to item 1, wherein, in the active position, a minimum gap between the wing and the handle is in the range of 25 to 35 mm.

3. An endoscope according to item 1, wherein the wing is rotatably connected to the handle to be movable through a rotary motion path about a wing rotation axis.

4. An endoscope according to item 3, wherein the insertion cord defines a longitudinal axis and said rotation axis is perpendicular to said longitudinal axis of the insertion cord.

5. An endoscope according to item 1, wherein the operating section comprises at least one rotary operating member rotatable about an operating member axis.

6. An endoscope according to item 5, wherein the rotary operating member is located on an opposite side of the handle as seen from the wing.

7. An endoscope according to item 5, wherein the wing rotation axis coincides with the operating member axis.

8. An endoscope according to item 1, wherein the length of the wing is in the range between 40 mm and 100 mm preferably between 50 mm and 85 mm.

9. An endoscope according to item 3, wherein at least one predetermined arresting position is provided along the rotary motion path.

10. An endoscope according to item 1, wherein the tip of the wing is resiliently deflectable away from the handle.

11. An endoscope according to item 1, wherein the wing comprises a core member with a Shore A hardness in the range of 75 to 120.

12. An endoscope according to item 11, where in the core member is covered by a softer coating.

13. An endoscope according to item 12, wherein the coating has a Shore A hardness in the range from 40 to 60.

14. A visualization system comprising a display device and an endoscope according to item 1 connectable to said display device.

The foregoing embodiments, variations and examples of the first aspect of the disclosure provide a wing with characteristics conceived to increase the comfortable use of the endoscope by a user. The user can adjust the position of the wing to suit the endoscopic procedure and the user's hand to further increase comfort. Some of the above-mentioned features may be present and others excluded. For example, the wing may have a core and an outer layer, but it can also comprise a core without an outer layer. The shape of the wing can be straight or bent. One or more arresting positions, comprising mating protrusions and recesses, may be provided. However, the retention force may also be provided without arresting positions, for example by providing stop surfaces at the first and second positions to limit further rotation without adding to the retention force provided by the textured surfaces.

We claim:

1. An endoscope comprising:

a handle;

an insertion cord extending distally from the handle;

a steering wheel rotatable about a steering wheel axis; and a wing rotatably connected to the handle opposite the steering wheel and with the handle between the wing and the steering wheel, the wing having a free end and being selectively rotatable about a wing rotation axis between a first arresting position and a second arresting position, wherein:

in the first arresting position the wing extends along the handle with the free end at a first distance to the handle to provide a hand space between the handle and the wing, the hand space being sufficient to fit a hand of an operator gripping the handle between the handle and the wing; and in the second arresting position the free end of the wing is moved away with respect to the handle and is positioned at a second distance to the handle, the second distance being larger than the first distance, wherein in the second arresting position the endoscope is devoid of the hand space.

2. The endoscope of claim 1, wherein the endoscope comprises a protrusion and a recess, one of the protrusion or the recess located on the handle and the other of the protrusion or the recess located on the wing, and wherein in the first arresting position the recess receives the protrusion.

3. The endoscope of claim 2, wherein the first arresting position is at most 90 degrees from the second arresting position along a rotary motion path.

4. The endoscope of claim 1, wherein in the first arresting position, the hand space comprises a minimum gap between the wing and the handle in a range of 25 to 35 mm.

5. The endoscope of claim 1, wherein the wing rotation axis is perpendicular to a longitudinal axis of the endoscope.

6. The endoscope of claim 1, wherein a length of the wing is in a range between 40 mm and 100 mm.

7. The endoscope of claim 6, wherein the length of the wing is in a range between 50 mm and 85 mm.

8. The endoscope of claim 1, wherein at least one predetermined arresting position is provided intermediate the first arresting position and the second arresting position along a rotary motion path.

9. The endoscope of claim 1, wherein the free end of the wing is resiliently deflectable away from the handle.

10. The endoscope of claim 1, wherein the wing comprises a core with a Shore A hardness in a range of 75 to 120.

11. The endoscope of claim 10, wherein the core is covered by a softer coating.

12. The endoscope of claim 11, wherein the coating has a Shore A hardness in a range from 40 to 60.

13. The endoscope of claim 1, wherein in the first arresting position, the hand space comprises a minimum gap between the wing and the handle in a range of 25 to 35 mm, and wherein a length of the wing is in a range between 40 mm and 100 mm.

14. An endoscope comprising:
a handle;
an insertion cord extending distally from the handle;
a steering wheel rotatable about a steering wheel axis; and
a wing rotatably connected to the handle opposite the steering wheel and with the handle between the wing and the steering wheel, the wing having a free end and being selectively rotatable about a wing rotation axis between a first arresting position and a second arresting position, wherein:
in the first arresting position the wing extends along the handle with the free end at a first distance to the handle to provide a hand space between the handle and the wing, the hand space being sufficient to fit a hand of an operator gripping the handle between the handle and the wing; and in the second arresting position the free end of the wing is moved away with respect to the handle and is positioned at a second distance to the handle, the second distance being larger than the first distance, wherein the endoscope comprises a protrusion and a recess, one of the protrusion or the recess located on the handle and the other of the protrusion or the recess located on the wing, and wherein in the first arresting position the recess receives the protrusion, and wherein the endoscope comprises a second protrusion and a second recess, one of the second protrusion or the second recess located on the handle and the other of the second protrusion or the second recess located on the wing, and wherein in the second arresting position the second recess receives the second protrusion.

15. The endoscope of claim 14, wherein the first arresting position is at most 90 degrees from the second arresting position along a rotary motion path.

16. The endoscope of claim 14, wherein in the second arresting position the endoscope is devoid of the hand space.

17. The endoscope of claim 16, wherein in the second arresting position the wing is perpendicular to a longitudinal axis of the endoscope.

18. An endoscope comprising:
a handle;
an insertion cord extending distally from the handle;
a steering wheel rotatable about a steering wheel axis; and
a wing rotatably connected to the handle opposite the steering wheel and with the handle between the wing and the steering wheel, the wing having a free end and being selectively rotatable about a wing rotation axis between a first arresting position and a second arresting position, wherein:
in the first arresting position the wing extends along the handle with the free end at a first distance to the handle to provide a hand space between the handle and the wing, the hand space being sufficient to fit a hand of an operator gripping the handle between the handle and the wing; and
in the second arresting position the free end of the wing is moved away with respect to the handle and is positioned at a second distance to the handle, the second distance being larger than the first distance, wherein the wing rotation axis is concentric with the steering wheel axis.

19. The endoscope of claim 18, wherein the wing rotation axis is perpendicular to a longitudinal axis of the endoscope.

20. A visualization system comprising:
a display device; and
the endoscope of claim 1, wherein the endoscope is connectable to said display device.

* * * * *